US012799087B2

(12) United States Patent
Gu et al.

(10) Patent No.: US 12,799,087 B2
(45) Date of Patent: Nov. 17, 2026

(54) METHOD FOR PREPARING KEY INTERMEDIATE OF ABT-737 AND METHOD FOR PREPARING ABT-737

(71) Applicant: Xeon Biopharmaceutical Limited, Suzhou (CN)

(72) Inventors: Yanfei Gu, Suzhou (CN); Yao He, Suzhou (CN)

(73) Assignee: Xeon Biopharmaceutical Limited, Suzhou (CN)

( * ) Notice: Subject to any disclaimer, the term of this patent is extended or adjusted under 35 U.S.C. 154(b) by 884 days.

(21) Appl. No.: 17/597,868

(22) PCT Filed: Jun. 17, 2021

(86) PCT No.: PCT/CN2021/100636
§ 371 (c)(1),
(2) Date: Dec. 4, 2023

(87) PCT Pub. No.: WO2022/246929
PCT Pub. Date: Dec. 1, 2022

(65) Prior Publication Data

US 2024/0140923 A1 May 2, 2024

(30) Foreign Application Priority Data

May 26, 2021 (CN) ......................... 202110575439.7

(51) Int. Cl.

| | |
|---|---|
| ***C07D 295/155*** | (2006.01) |
| ***C07C 227/18*** | (2006.01) |
| ***C07C 303/40*** | (2006.01) |
| ***C07C 319/14*** | (2006.01) |
| ***C07C 319/20*** | (2006.01) |

(52) U.S. Cl.
CPC ........ *C07D 295/155* (2013.01); *C07C 227/18* (2013.01); *C07C 303/40* (2013.01); *C07C 319/14* (2013.01); *C07C 319/20* (2013.01)

(58) Field of Classification Search
CPC . C07D 295/155; C07C 227/18; C07C 303/40; C07C 319/14; C07C 319/20
USPC .......................................................... 544/393
See application file for complete search history.

(56) References Cited

FOREIGN PATENT DOCUMENTS

| | | | |
|---|---|---|---|
| CN | 101535280 | A | 9/2009 |
| CN | 101641338 | A | 2/2010 |
| CN | 101798292 | A | 8/2010 |
| CN | 103153954 | A | 6/2013 |
| WO | 2009036035 | A1 | 3/2009 |
| WO | 2009036051 | A1 | 3/2009 |

OTHER PUBLICATIONS

Patent Cooperation Treaty, International Search Report for International Application PCT/CN2021/100636, Dated Feb. 24, 2022.

*Primary Examiner* — Kahsay Habte
(74) *Attorney, Agent, or Firm* — Luedeka Neely, P.C.; Mark P. Crockett

(57) ABSTRACT

A method for preparing a key intermediate of ABT-737 and a method for preparing ABT-737 are disclosed. In the method, the compound having a structure represented by formula I is used as the starting material. The carboxyl group in the compound having a structure represented by formula I is first reduced to a hydroxyl group, followed by a vulcanization by a vulcanizing agent, and then an amination, a deprotection, a condensation, and a carbonyl group reduction, to obtain the key intermediate of ABT-737 having a structure represented by formula VI. Tert-butoxycarbonyl is used as the protecting group for the compound having a structure represented by formula I, and the subsequent intermediate containing the protecting group of tert-butoxycarbonyl is stable, and easy to be deprotected.

formula I

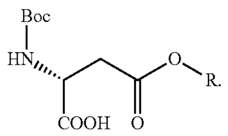

12 Claims, 1 Drawing Sheet

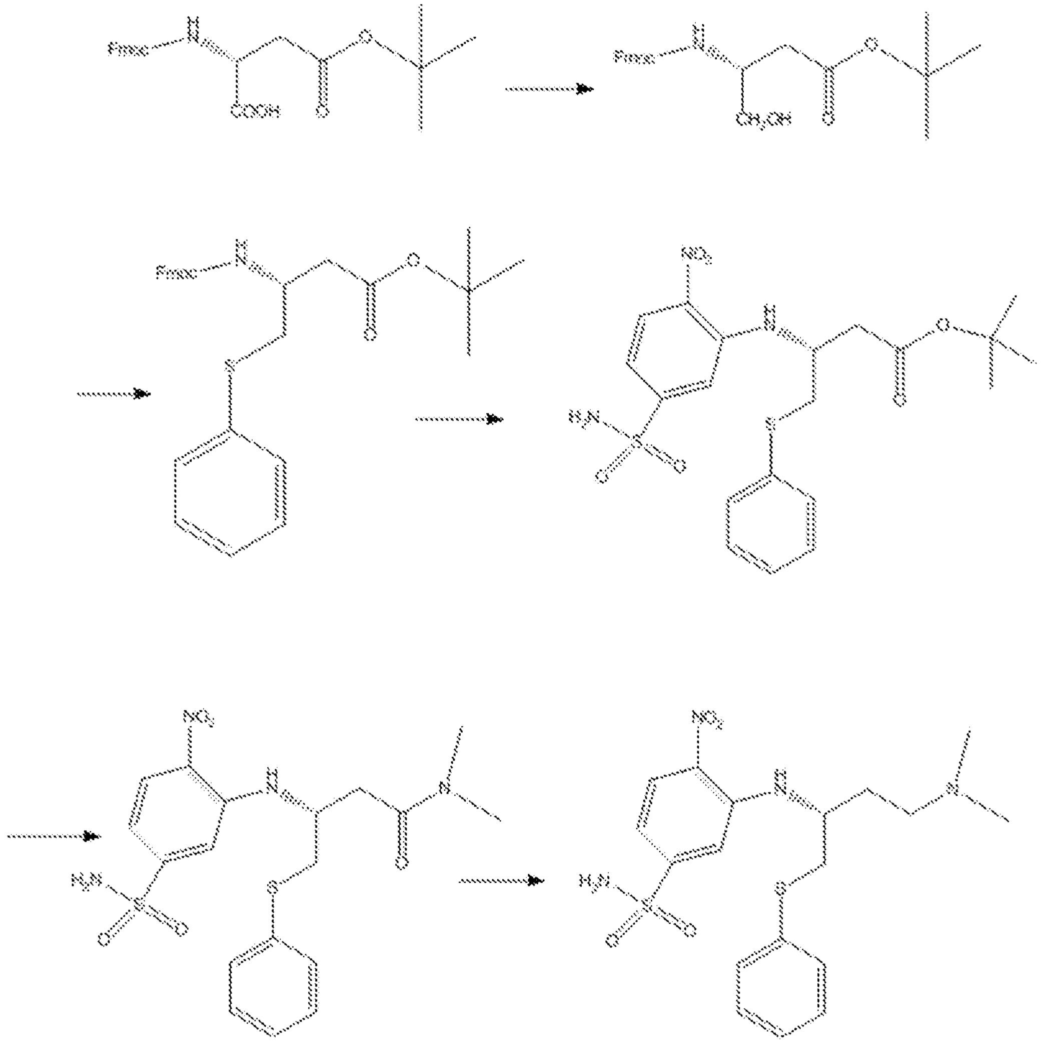

METHOD FOR PREPARING KEY INTERMEDIATE OF ABT-737 AND METHOD FOR PREPARING ABT-737

This patent application claims the benefit and priority of Chinese Patent Application No. 202110575439.7, entitled "method for preparing key intermediate of ABT-737 and method for preparing ABT-737", filed on May 26, 2021, the disclosure of which is incorporated by reference herein in its entirety as part of the present application.

TECHNICAL FIELD

The present disclosure relates to the technical field of drug synthesis, in particular to a method for preparing a key intermediate of ABT-737 and a method for preparing ABT-737.

BACKGROUND ART

Benzamide compound ABT-737 (chemical name: 4-[4-[(4'-chloro[1,1'-biphenyl]-2-yl]methyl]-1-piperazinyl]-N-[[4-[[(1R)-3-(dimethylamino)-1-[((phenylthio)methyl]propyl]amino]-3-nitrophenyl]sulfonyl]benzamide; CAS No. 852808-04-9) is a new and effective inhibitor for BCL-2 family proteins. It has high affinity for BCL-XL, BCL-2 and BCL-w, but has no affinity for BCL-B, MCL-1 and A1 which have lower homology. However, in fact, BCL-2 family proteins are critical to the survival and overexpression of many tumor cells. ABT-737 has monotherapy activity against lymphoma, small cell lung cancer, and myeloma in vitro and in vivo. Recent studies have shown that ABT-737 could effectively kill acute myeloid leukemia cells, progenitor cells, and stem cells, while retaining intact hematopoietic cells. ABT-737 could disrupt the BCL-2/BAX complex and activate the intrinsic apoptotic pathway in a BAK-dependent rather than BIM-dependent manner.

At present, in the prior art, the key intermediate of ABT-737 is usually prepared first, and then ABT-737 is obtained through a condensation reaction. The common method for preparing the key intermediate of ABT-737 is as follows: taking N-fluorenylmethoxycarbonyl-D-aspartate-4-tert-butyl ester as the starting material; subjecting it to a reduction by sodium borohydride, a vulcanization by thiophenol, a FMOC-deprotection under an alkaline condition; subjecting the deprotected product to a condensation with 3-nitro-4-fluorobenzenesulfonamide; hydrolyzing the condensation product by using lithium hydroxide, subjecting the hydrolysate to an amination, and finally reducing to obtain the key intermediate of ABT-737. The specific route is shown in FIG. 1.

In the above scheme, the N-fluorenylmethyloxycarbonyl group is used as the protective group. However, the intermediate with the protective group of N-fluorenylmethyloxycarbonyl group exhibits poor stability, and thus it is difficult to synthesize in large quantities, and the product yield is low.

SUMMARY

In view of this, an object of the present disclosure is to provide a method for preparing a key intermediate of ABT-737 and a method for preparing ABT-737. In the present disclosure, the key intermediates of ABT-737 are synthesized by using the starting material containing the tert-butoxycarbonyl protective group, the reaction intermediate is stable, which is easy to synthesize in large quantities, and the yield of the product is high.

In order to achieve the above object, the present disclosure provides the following technical solutions:

The present disclosure provides a method for preparing a key intermediate of ABT-737, comprising the following steps:

(1) subjecting a compound having a structure represented by formula I and an activator to an esterification reaction to obtain an active ester, subjecting the active ester and a first reducing agent to a reduction reaction to obtain a compound having a structure represented by formula II, formula I

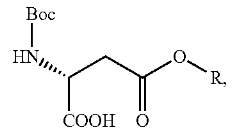

formula II

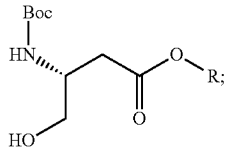

(2) subjecting the compound having a structure represented by formula II, a vulcanizing agent, and an organic phosphine to a vulcanization reaction to obtain a compound having a structure represented by formula III, wherein the vulcanizing agent includes one or more selected from the group consisting of a thiophenol metal salt and diphenyl disulfide, formula III

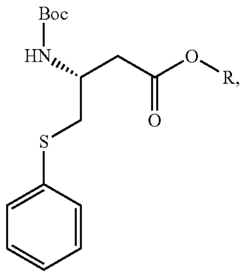

in formula I to formula III, R represents a chain alkyl group or cycloalkyl group;

(3) subjecting the compound having a structure represented by formula III to a hydrolysis reaction under an alkaline condition to obtain a hydrolysate, and subjecting the hydrolysate and dimethylamine to an amination reaction to obtain a compound having a structure represented by formula IV, formula IV

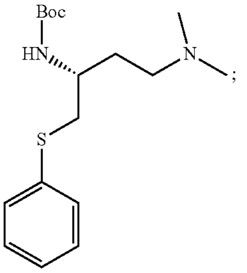

(4) subjecting the compound having a structure represented by formula IV to a deprotection reaction with a deprotection reagent to obtain a deprotected product, and subjecting the deprotected product to a condensation reaction with 3-nitro-4-halobenzenesulfonamide to obtain a compound having a structure represented by formula V;

formula V

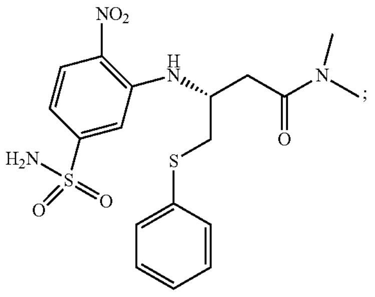

and (5) subjecting the compound having a structure represented by formula V and a second reducing agent to a carbonyl reduction reaction under an acidic condition to obtain the key intermediate of ABT-737 having a structure represented by formula VI, formula VI

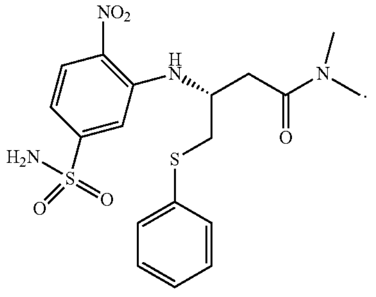

In some embodiments, the activator includes N-hydroxysuccinimide and/or isobutyl chloroformate. In some embodiments, a molar ratio of the compound having a structure represented by formula I to the activator is in the range of 1:(1-1.2).

In some embodiments, the esterification reaction is conducted at a temperature of −20° C. to 0° C. for 20-25 h.

In some embodiments, the esterification reaction is carried out under the catalysis of a catalyst, and the catalyst is an organic amine. In some embodiments, a molar ratio of the compound having a structure represented by formula I to the catalyst is in the range of 1:(1.05-1.5).

In some embodiments, in step (1), the first reducing agent is a boron reducing agent. In some embodiments, a molar ratio of the active ester to the first reducing agent is in the range of 1:(1.5-2).

In some embodiments, the reduction reaction is carried out in a mixed solvent, and the mixed solvent includes one or more of a tetrahydrofuran-water mixed solvent, a tetrahydrofuran-methanol mixed solvent, and a methanol-water mixed solvent.

In some embodiments, the reduction reaction is conducted at a temperature of −5° C. to 20° C. for 5-20 min.

In some embodiments, a molar ratio of the compound having a structure represented by formula II to the vulcanizing agent is in the range of 1:(1.2-2).

In some embodiments, the organic phosphine includes one or more of tributyl phosphine, triphenyl phosphine, and tricarboxyethyl phosphine. In some embodiments, a molar ratio of the compound having a structure represented by formula II to the organic phosphine is in the range of 1:(1.2-2).

In some embodiments, the vulcanization reaction is conducted at a temperature 70-85° C. for 15-20 h.

In some embodiments, in step (3), the alkaline condition is provided by an inorganic base.

In some embodiments, a molar ratio of the compound having a structure represented by formula III to the inorganic base is in the range of 1:(2-4).

In some embodiments, the hydrolysis reaction is conducted at room temperature, for 20-24 h.

In some embodiments, the amination reaction is carried out under the conditions of a condensing agent and a catalyst, wherein the condensing agent includes dicyclohexylcarbodiimide and/or 3-(ethyliminomethylideneamino)-N,N-dimethylpropan-1-amine hydrochloride, and the catalyst includes 4-dimethylaminopyridine and/or N,N-diisopropylethylamine.

In some embodiments, a molar ratio of the hydrolysate, the condensing agent, and the catalyst is in the range of 1:(1.8-2.5):(2-2.2).

In some embodiments, a molar ratio of the hydrolysate to dimethylamine is in the range of 1:(1.5-2.5).

In some embodiments, the amination reaction is conducted at room temperature for 20-30 h.

In some embodiments, the deprotection reagent is one or more selected from the group consisting of aqueous hydrochloric acid solution, hydrogen chloride-methanol solution, hydrogen chloride-ethyl acetate solution, and trifluoroacetic acid.

In some embodiments, the deprotection reaction is conducted at room temperature for 2-5 h.

In some embodiments, a molar ratio of the deprotected product to 3-nitro-4-halobenzenesulfonamide is in the range of 1:(1.05-1.3).

In some embodiments, the condensation reaction is conducted at a temperature of 20-30° C. for 20-30 h.

In some embodiments, in step (5), the second reducing agent is a boron reducing agent; the acidic condition is provided by an acidic reagent, and the acidic reagent includes hydrochloric acid and/or trifluoroacetic acid.

In some embodiments, the carbonyl reduction reaction is conducted specifically as follows:mixing a compound having a structure represented by formula V and a boron reducing agent, and subjecting the resulting mixture to a complexation reaction to obtain a boron complex; mixing the boron complex and an acidic reagent and subjecting the resulting mixture to a hydrolysis reaction to obtain the compound having a structure represented by formula VI.

In some embodiments, step (4) is replaced by step (4'), and step (5) is replaced by (5'):

(4') under the actions of the second reducing agent and the acidic reagent, subjecting the compound having a structure represented by formula IV to a carbonyl reduction reaction to obtain a compound having a structure represented by formula V', formula V'

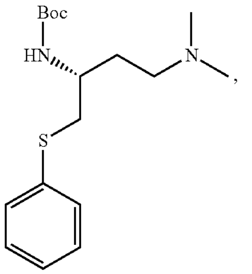

and (5') under the action of the deprotection reagent, subjecting the compound having a structure represented by formula V' to a deprotection reaction to obtain a deprotected product, and subjecting the deprotected product to a condensation reaction with 3-nitro-4-halobenzenesulfonamide to obtain the key intermediate of ABT-737.

The present disclosure also provides a method for preparing ABT-737, comprising the following steps:

preparing the key intermediate of ABT-737 according to the method as described in the above technical solution;

mixing the key intermediate of ABT-737 with 4-(4-((4'-chloro-[1,1'-biphenyl]-2-yl) methyl) piperazin-1-yl) benzoic acid and subjecting the mixture to a condensation reaction to obtain ABT-737 having a structure represented by formula VII, formula VII

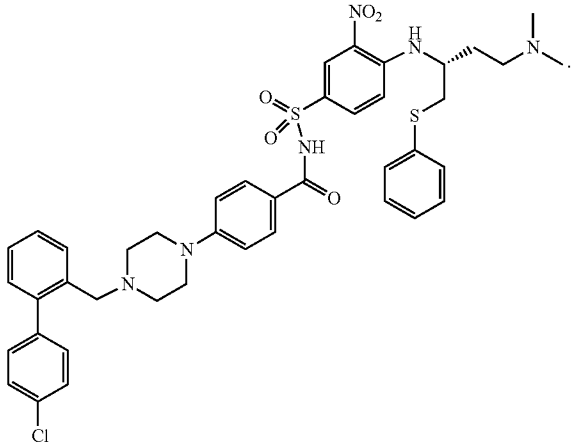

In some embodiments, a molar ratio of the key intermediate of ABT-737 to 4-(4-((4'-chloro-[1,1'-biphenyl]-2-yl) methyl piperazin-1-yl) benzoic acid is in the range of 1:(1.05-1.1).

In some embodiments, the condensation reaction is carried out under the actions of a condensing agent and a catalyst, wherein the condensing agent is dicyclohexylcarbodiimide and/or 3-(ethyliminomethylideneamino)-N,N-dimethylpropan-1-amine hydrochloride, and the catalyst is 4-dimethylaminopyridine and/or N,N-diisopropylethylamine.

In some embodiments, a molar ratio of the key intermediate of ABT-737, the condensing agent, and the catalyst is in the range of 1:(2-2.5):(2-2.5), and more preferably 1:2.1:2.1.

In some embodiments, the condensation reaction is performed at room temperature for 40-60 h.

The present disclosure provides a method for preparing a key intermediate of ABT-737, and the compound having a structure represented by formula I is used as a starting material in the present disclosure. First, the carboxyl group in the compound having a structure represented by formula I is reduced to a hydroxyl group, then subjected to a vulcanization reaction with the vulcanizing agent, and then subjected to amination, deprotection, condensation and carbonyl reduction reaction to obtain the key intermediate of ABT-737 having a structure represented by formula VI. The compound having a structure represented by formula I has tert-butoxycarbonyl as the protecting group, and the resulting intermediate containing the protecting group of tert-butoxycarbonyl is stable and easy to be deprotected, which is easy to synthesize in large quantities, and the yield of the key intermediate of ABT-737 is high.

Further, when preparing key intermediates of ABT-737 by traditional methods, high toxic reagents such as methanesulfonyl chloride and thiophenol are needed in the vulcanization reaction, which is difficult to operate. However, in the vulcanization process of the present disclosure, thiophenol metal salt and diphenyl disulfide are used as a vulcanizing reagent, which are low-toxic and stable under normal temperature and pressure. Compared with traditional methods, the method according to the present disclosure could avoid the use of toxic and harmful reagents, is simpler in operation, and could greatly reduce the production cost, thereby having a good industrialization prospect.

In addition, in the traditional method, the vulcanized product is first deprotected, and then condensed with 3-nitro-4-halobenzenesulfonamide, because the FMOC protecting group is easily removed under alkaline conditions. Thus, it is necessary to produce a stable product preferentially, and the stable product is then subjected to an amination and a carbonyl reduction reaction, while in the scheme of the present disclosure, a starting material with a BOC protecting group is used, and the BOC protecting group is not sensitive under alkaline conditions. The raw material is first reduced and vulcanized, the vulcanized product is aminated, and then subjected to a deprotection, condensation and carbonyl reduction reaction. The yield of the carboxylic acid reduction step in the present disclosure is twice larger than that of the conventional method in which FMOC functions as the protecting group. Also, for the conventional method, in which deprotection and condensation reactions are performed before the hydrolysis reaction, amination reaction, and carbonyl reduction reaction, 3-nitro-4-halobenzenesulfonamide group, which is introduced, is more polar, and thus it is difficult to purify the product by the column chromatography. Therefore, in the present disclosure, 3-nitro-4-halobenzenesulfonamide group is introduced in the last step or the last two steps, which could greatly reduce the amount of solvents used during the column chromatography and reduce cost.

Further, in the method of the present disclosure, the carbonyl group in the aminated product may be first reduced, and then subjected to a deprotection and condensation reaction. The synthetic route is more flexible, easy to operate, and could further improve the product yield.

Further, the method according to the present disclosure could be performed under mild reaction conditions, and reagents used is low in cost.

The results of the examples show that in the method for preparing the key intermediate of ABT-737 of the present disclosure, the compound having a structure represented by formula II is prepared from the compound having a structure represented by formula I, with a yield of not less than 61%, the compound having a structure represented by formula III is prepared from the compound having a structure represented by formula II, with a yield of not less than 85%, and the compound having a structure represented by formula IV is prepared from the compound having a structure represented by formula III, with a yield of around 90%, and the compound having a structure represented by formula V is prepared from the compound having a structure represented by formula IV, with a yield of 90%, and finally the key intermediate of ABT-737 is prepared from the compound having a structure represented by formula V, with a yield of not less than 68%. Where the carbonyl group is first reduced and then subjected to a deprotection and condensation reaction, the compound having a structure represented by formula V' is prepared from the compound having a structure represented by formula IV, with a yield of not less than 76%, and the key intermediate of ABT-737 is prepared from the compound having a structure represented by formula V', with a yield of not less than 85%.

The present disclosure also provides a method for preparing ABT-737, in which, the key intermediate of ABT-737 is prepared by the method described in the above scheme, and then subjected to a condensation reaction to obtain ABT-737, having a structure represented by formula VII. The results of the examples show that the purity of the product prepared by the method of the present disclosure is not less than 99.1%, and the yield is not less than 55%.

BRIEF DESCRIPTION OF THE DRAWINGS

FIG. 1 is a diagram showing a synthetic route for the synthesis of a key intermediate of ABT-737 in the prior art in this field.

DETAILED DESCRIPTION OF THE EMBODIMENTS

The present disclosure discloses a method for preparing a key intermediate of ABT-737, comprising the following steps:

(1) subjecting a compound having a structure represented by formula I and an activator to an esterification reaction to obtain an active ester, subjecting the active ester and a first reducing agent to a reduction reaction to obtain a compound having a structure renresented by formula IL formula I

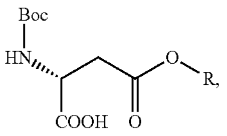

-continued formula II

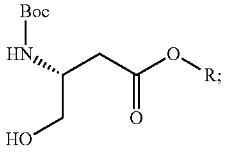

(2) subjecting the compound having a structure represented by formula II, a vulcanizing agent, and an organic phosphine to a vulcanization reaction to obtain a compound having a structure represented by formula III, wherein the vulcanizing agent includes one or more of thiophenol metal salt and diphenyl disulfide, formula III

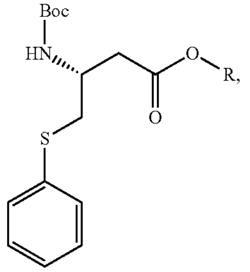

in formula I to formula III, R represents a chain alkyl group or cycloalkyl group; in some embodiments, the chain alkyl group contains not more than 8 carbon atoms, preferably 1-6 carbon atoms; in some embodiments, the chain alkyl group is specifically methyl, ethyl, or isobutyl; In some embodiments, the cycloalkyl group contains 5-8 carbon atoms; in some embodiments, the cycloalkyl group is specifically cyclopentyl methyl, or cyclohexyl methyl;

(3) subjecting the compound having a structure represented by formula III to a hydrolysis reaction under an alkaline condition to obtain a hydrolysate, and subjecting the hydrolysate and dimethylamine to an amination reaction to obtain a compound having a structure represented by formula IV;

formula IV

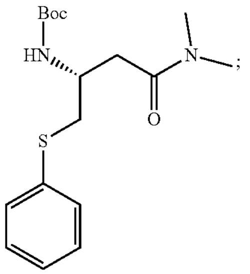

(4) subjecting the compound having a structure represented by formula IV to a deprotection reaction with a deprotection reagent to obtain a deprotected product, and subjecting the deprotected product to a condensation reaction with 3-nitro-4-halobenzenesulfonamide to obtain a compound having a structure represented by formula V, formula V

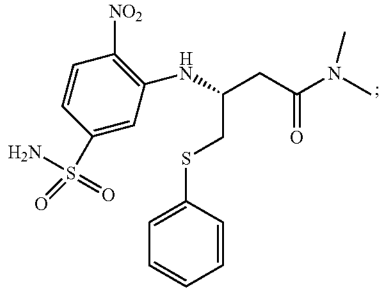

and (5) subjecting the compound having a structure represented by formula V and a second reducing agent to a carbonyl reduction reaction under an acidic condition to obtain the key intermediate of ABT-737 having a structure represented by formula VI, formula VI

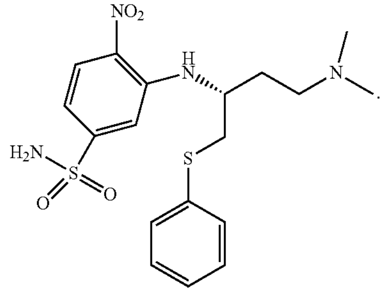

In the present disclosure, the compound having a structure represented by formula I and the activator are subjected to an esterification reaction to obtain an active ester. In some embodiments of the present disclosure, the activator includes N-hydroxysuccinimide and/or isobutyl chloroformate. In some embodiments, the molar ratio of the compound having a structure represented by formula I to the activator is in the range of 1:(1-1.2), and more preferably 1:1.1. In some embodiments, the catalyst for the esterification reaction is an organic amine, and more preferably one or more of dicyclohexylcarbodiimide, triethylamine, and N,N-diisopropylethylamine. In some embodiments, the molar ratio of the compound having a structure represented by formula I to the catalyst is in the range of 1:(1.05-1.5), and more preferably 1:(1.1-1.2). In some embodiments of the present disclosure, the solvent for the esterification reaction is one or more selected from the group consisting of ethyl acetate, dichloromethane, and tetrahydrofuran. In the present disclosure, there is no special requirement for the amount of the solvent used for the esterification reaction, as long as the esterification reaction could proceed smoothly. In the present disclosure, there is no special requirement for the source of the compound having a structure represented by formula I, and it may be a commercially available product or prepared by using a method well known to those skilled in the art. In specific embodiments of the present disclosure, the compound having a structure represented by formula I is purchased from Shanghai Bi De Pharmaceutical Reagent Company.

In some embodiments of the present disclosure, the esterification reaction is conducted at a temperature of −20° C. to 0° C., and more preferably −5° C. to 0° C. In some embodiments, the esterification reaction is conducted for 20-25 h, and more preferably 22-24 h.

In the present disclosure, where the activator is N-hydroxysuccinimide, the structural formula of the active ester is as shown in formula i, where the activator is isobutyl chloroformate, and the structural formula of the active ester is shown in formula ii:

formula i

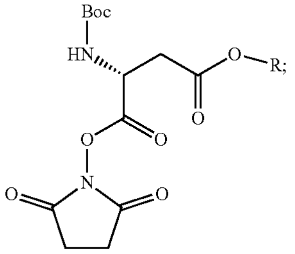

formula ii

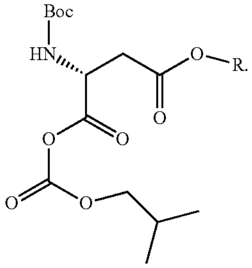

The reduction of the carboxyl group to the alcohol group requires a strong reducing agent, if the strong reducing agent is used directly, the ester group at the other end of the compound having a structure represented by formula I is easily reduced. In the present disclosure, the compound having a structure represented by formula I is subjected to an esterification reaction to generate an active ester, and the active ester is then subjected to a reduction reaction, which enables the reduction reaction to proceed rapidly and meanwhile reduces the influence on the ester group.

In some specific embodiments of the present disclosure, the compound having a structure represented by formula I is first dissolved in a solvent, then the atmosphere therein is replaced with nitrogen, and the system is cooled to not higher than 0° C.; the active agent is added thereto, and then the catalyst solution is added dropwise thereto; the resulting mixture is maintained at the esterification reaction temperature and subjected to the reaction. In some embodiments, the solvent used in the catalyst solution is the same as the solvent used in the esterification reaction, which will not be repeated here. In some embodiments, the concentration of the catalyst solution is in the range of 0.19-0.3 g/mL. and the time for the esterification reaction starts counting from the completion of the catalyst solution dripping. In some specific embodiments of the present disclosure, it is preferable to confirm the disappearance of the raw materials by TLC detection, and then the reaction is considered to be completed. In some embodiments, the reagent used in the TLC detection is a mixed reagent of dichloromethane, methanol, and acetic acid, and the volume ratio of dichloromethane, methanol, and acetic acid is 4:0.2:0.1.

In some embodiments, after the esterification reaction is completed, the obtained product mixed liquid is subjected to a post-treatment to obtain an active ester. In some embodiments of the present disclosure, the post-treatment is conducted as follows: filtering the obtained product mixed liquid, mixing the filtrate and a saturated sodium carbonate solution to wash the filtrate, and layering the resulting mixture, to obtain an aqueous layer; subjecting the aqueous layer to an extraction with an organic solvent to obtain an organic phase, subjecting the organic phase to a washing with saturated brine, a drying with anhydrous sodium sulfate, a filtration, and a spin-drying in sequence to obtain the active ester. In some embodiments, the organic solvent for extraction is ethyl acetate.

After the active ester is obtained, the active ester and the first reducing agent are subjected to a reduction reaction to obtain the compound having a structure represented by formula II. In some embodiments of the present disclosure, the first reducing agent is a boron reducing agent, and the boron reducing agent includes one or more selected from the group consisting of sodium borohydride, potassium borohydride, borane, and a borane derivative solution. In some embodiments, the borane derivative solution is a borane-tetrahydrofuran solution, and the concentration of the borane-tetrahydrofuran solution is 1 mol/L. In the present disclosure, there is no special requirement for the source of the borane-tetrahydrofuran solution, and a commercially available product may be used. In some embodiments of the present disclosure, a molar ratio of the active ester to the first reducing agent is in the range of 1:(1.5-2), and under the condition that the first reducing agent is a borane derivative solution, the molar amount of the first reducing agent is calculated as the molar amount of solute in the solution.

In some embodiments of the present disclosure, the reduction reaction is carried out in a mixed solvent, and the mixed solvent includes one or more selected from the group consisting of a tetrahydrofuran-water mixed solvent, a tetrahydrofuran-methanol mixed solvent, and a methanol-water mixed solvent, and more preferably a tetrahydrofuran-water mixed solvent. In some embodiments, a volume ratio of tetrahydrofuran to water in the tetrahydrofuran-water mixed solvent is in the range of (5-8):1, and more preferably (7-7.5):1. In the present disclosure, there is no special requirement on the amount of the mixed solvent, as long as the reduction reaction could proceed smoothly.

In some embodiments of the present disclosure, the reduction reaction is conducted at temperature of −5° C. to 20° C., and more preferably 0-10° C. In some embodiments, the reduction reaction is conducted for 5-20 min, and more preferably 5-10 min.

In some specific embodiments of the present disclosure, the first reducing agent is added to the solvent for the reduction reaction in an ice bath to obtain a first reducing agent solution; the active ester is dissolved in an organic solvent to obtain an active ester solution; the active ester solution is added dropwise to the first reducing agent solution and the resulting mixture is subjected to a reduction reaction at a temperature for the reduction reaction. In some embodiments, the organic solvent for dissolving the active ester is tetrahydrofuran. In some embodiments, the time for the reduction reaction starts counting from the completion of the dripping of the active ester solution. In some embodiments of the present disclosure, the completion of the reaction of the active ester is confirmed by a TLC detection. In some embodiments, the reagent used for the TLC detection is a dichloromethane-methanol mixed reagent or a dichloromethane-ethyl acetate mixed reagent. In some embodiments, the volume ratio of dichloromethane to methanol in the dichloromethane-methanol mixed reagent is 20:1, and the volume ratio of dichloromethane to ethyl acetate in the dichloromethane-ethyl acetate mixed reagent is 3:2.

In some embodiments, after the reduction reaction is completed, the obtained product mixed liquid is subjected to a post-treatment to obtain the compound having a structure represented by formula II. In some embodiments of the present disclosure, the post-treatment includes the following steps:adding a saturated aqueous ammonium chloride solution to the reduction reaction solution to quench the reaction, subjecting the resulting product mixed liquid to an extraction with ethyl acetate to obtain an organic phase, and subjecting the organic phase to a washing with saturated brine, a drying with anhydrous sodium sulfate, a spin-drying, and a purification by column chromatography to obtain the compound having a structure represented by formula II. In some embodiments, the extractions is conducted 2 times, and the organic phases obtained from the two extractions are combined. In some embodiments, the reagent for column chromatography is a mixed solvent of petroleum ether and ethyl acetate. In some embodiments, the volume ratio of petroleum ether to ethyl acetate in the mixed solvent is 3:1.

After obtaining the compound having a structure represented by formula II, the compound having a structure represented by formula II, the vulcanizing agent, and the organic phosphine are subjected to a vulcanization reaction to obtain the compound having a structure represented by formula III. In the present disclosure, the vulcanizing agent includes one or more of a thiophenol metal salt and diphenyl disulfide, and in some embodiments, the thiophenol metal salt includes one or more selected from the group consisting of lithium thiophenoxide, potassium thiophenoxide, and sodium thiophenoxide. In specific embodiments of the present disclosure, the vulcanizing agent is diphenyl disulfide. In some embodiments, the molar ratio of the compound having a structure represented by formula II to the vulcanizing agent is in the range of 1:(1.2-2). In some embodiments, the organic phosphine includes one or more selected from the group consisting of tributylphosphine, triphenylphosphine, and tricarboxyethylphosphine. In some embodiments, the molar ratio of the compound having a structure represented by formula II to the organic phosphine is in the range of 1:(1.2-2), and more preferably 1:1.5. In some embodiments, the solvent for the vulcanization reaction is one or more selected from the group consisting of toluene, acetonitrile, dioxane, and N,N-dimethylformamide, and more preferably toluene.

In some embodiments of the present disclosure, the vulcanization reaction is conducted at temperature of 70-85° C., and more preferably 78-82° C. In some embodiments, the vulcanization reaction is conducted for 15-20 h, and more preferably 18-20 h.

In specific embodiments of the present disclosure, the compound having a structure represented by formula II is dissolved in the solvent for vulcanization reaction, and then diphenyl disulfide and organic phosphine are added thereto in sequence; the atmosphere is replaced with nitrogen; the resulting mixture is subjected to a vulcanization reaction at a constant temperature in an oil bath. In some embodiments, the vulcanization reaction is carried out under closed conditions. In some embodiments of the present disclosure, TLC detection is used to confirm the completion of vulcanization reaction. In some embodiments, the reagent used in the TLC detection is a dichloromethane-methanol mixed solvent. In some embodiments, the volume ratio of dichloromethane to methanol in the mixed solvent is 20:1.

In some embodiments, after the vulcanization reaction is completed, the obtained product mixed liquid is subjected to a post-treatment to obtain a compound having a structure represented by formula III. In some embodiments of the present disclosure, the post-treatment includes the following steps: concentrating the obtained product mixed liquid to remove the solvent, and purifying the concentrated product mixture by column chromatography to obtain the compound having a structure represented by formula III. In some embodiments, the reagent for column chromatography is a mixed solvent of petroleum ether and ethyl acetate, and the volume ratio of petroleum ether to ethyl acetate in the mixed solvent is 10:1.

After obtaining the compound having a structure represented by formula III, the compound having a structure represented by formula III is subjected to a hydrolysis reaction under alkaline conditions to obtain the hydrolysate. In the present disclosure, the alkaline condition is provided by an inorganic base. In some embodiments, the inorganic base is one or more of lithium hydroxide, sodium hydroxide, potassium hydroxide, and potassium carbonate. In specific embodiments of the present disclosure, the lithium hydroxide is lithium hydroxide monohydrate. In some embodiments, the molar ratio of the compound having a structure represented by formula III to the inorganic base is in the range of 1:(2-4), and more preferably 1:3. In some embodiments, the solvent for the hydrolysis reaction is methanol. In the present disclosure, there is no special requirement for the amount of the solvent for the hydrolysis reaction, as long as the hydrolysis reaction could proceed smoothly.

In some embodiments of the present disclosure, the hydrolysis reaction is conducted at room temperature. In some embodiments, the hydrolysis reaction is conducted for 20-24 h, and more preferably 22-23 h.

In specific embodiments of the present disclosure, it is preferable that the compound having a structure represented by formula III is dissolved in the solvent for the hydrolysis reaction, and then an inorganic base is added thereto, and the resulting solution is subjected to a hydrolysis reaction.

In some embodiments, after the hydrolysis reaction is completed, the obtained product mixed liquid is subjected to a post-treatment to obtain a hydrolysate. In some embodiments of the present disclosure, the post-treatment includes the following steps: mixing the obtained product mixed liquid with the weakly acidic solution, and subjecting the obtained mixed solution to an extraction with ethyl acetate to obtain an organic phase; subjecting the organic phase to a washing with saturated brine, a drying with anhydrous sodium sulfate, and a spin-drying in sequence to obtain a hydrolysate. In some embodiments of the present disclosure, the weakly acidic solution is 0.1 mol/L diluted aqueous hydrochloric acid solution, saturated aqueous sodium dihydrogen phosphate solution, 0.5 mol/L aqueous acetic acid solution or saturated aqueous potassium dihydrogen phosphate solution. In the present disclosure, a weakly acidic solution is used to neutralize the remaining base in the hydrolysis reaction, and the acidity of the solution is controlled to avoid the removal of the protecting group in the hydrolysate. In some embodiments of the present disclosure, the extraction is performed 3 times, and the organic phases obtained from the three extractions are combined.

After obtaining the hydrolysate, the hydrolysate and dimethylamine are subjected to an amination reaction to obtain a compound having a structure represented by formula IV. In some embodiments of the present disclosure, the amination reaction is carried out under the conditions of a condensing agent and a catalyst, and in some embodiments, the condensing agent includes dicyclohexylcarbodiimide and/or 3-(ethyliminomethylideneamino)-N,N-dimethylpropan-1-amine hydrochloride, and the catalyst includes 4-dimethylaminopyridine and/or N,N-diisopropylethylamine. In some embodiments, the molar ratio of the hydrolysate, the condensing agent, and the catalyst is in the range of 1:(1.8-2.5):(2-2.2), and more preferably 1:2:2. In some embodiments of the present disclosure, the molar ratio of the hydrolysate to dimethylamine is in the range of 1:(1.5-2.5). In some embodiments, the solvent for the amination reaction is dichloromethane. In the present disclosure, there is no special requirement for the amount of solvent used in the amination reaction, as long as the amination reaction could proceed smoothly.

In some embodiments of the present disclosure, the amination reaction is performed at room temperature. In some embodiments, the amination reaction is performed for 20-30 h, and more preferably for 24-25 h.

In specific embodiments of the present disclosure, it is preferable that the obtained hydrolysate is mixed with the dimethylamine solution, and then the condensing agent, a catalyst, and a solvent for the amination reaction are added in sequence, and the resulting mixture is subjected to an amination reaction. In some embodiments, the solvent of the dimethylamine solution is tetrahydrofuran. In some embodiments of the present disclosure, TLC detection is used to monitor the complete consumption of raw materials, and the reagent for TLC monitor is a mixed solvent of dichloromethane, methanol, and acetic acid, and the volume ratio of dichloromethane, methanol, and acetic acid in the mixed solvent is 4:0.2:0.1.

In some embodiments, after the amination reaction is completed, the obtained product mixed liquid is subjected to a post-treatment to obtain a compound having a structure represented by formula IV. In some embodiments of the present disclosure, the post-treatment includes the following steps: washing the obtained product mixed liquid with an aqueous hydrochloric acid solution and saturated brine in sequence, drying the washed liquid with anhydrous sodium sulfate, then filtering the dried liquid, concentrating, and purifying by column chromatography to obtain the compound having a structure represented by formula IV. In some embodiments, the concentration of the aqueous hydrochloric acid solution is 1 mol/L. In some embodiments, the reagent for column chromatography is a mixed solvent of petroleum ether and ethyl acetate. In some embodiments, the volume ratio of petroleum ether to ethyl acetate in the mixed solvent is 2:1.

After obtaining the compound having a structure represented by formula IV, the compound having a structure represented by formula IV and a deprotection reagent are subjected to a deprotection reaction to obtain a deprotected product. In some embodiments of the present disclosure, the deprotection reagent is one or more of an aqueous hydrochloric acid solution, a hydrogen chloride-methanol solution, a hydrogen chloride-ethyl acetate solution, and trifluoroacetic acid. In some embodiments, the concentration of the aqueous hydrochloric acid solution is 4-10 mol/L, and more 4-5 mol/L. In some embodiments, the concentration of the hydrogen chloride-methanol solution is 2 mol/L. In some embodiments, the concentration of the hydrogen chloride-ethyl acetate solution is 2 mol/L. In some embodiments, the molar ratio of the compound having a structure represented by formula IV to the deprotection reagent is in the range of 1:(30-35), and the molar amount of the deprotection reagent is calculated as the molar amount of the solute.

In some embodiments of the present disclosure, the solvent used for the deprotection reaction is one or more of dioxane, tetrahydrofuran and N,N-dimethylformamide. In the present disclosure, there is no special requirement for the amount of solvent used in the deprotection reaction, as long as the deprotection reaction could proceed smoothly.

In some embodiments of the present disclosure, the deprotection reaction is conducted at room temperature. In some embodiments, the deprotection reaction is conducted for 2-5 h, and more preferably for 2-3 h.

In specific embodiments of the present disclosure, it is preferable that the compound having a structure represented by formula IV, the solvent for the deprotection reaction, and the deprotection reagent are mixed directly, and the resulting mixture is subjected to a deprotection reaction.

In some embodiments, after the deprotection reaction is completed, the obtained product mixed liquid is subjected to a post-treatment to obtain the deprotected product. In some embodiments of the present disclosure, the post-treatment includes the following steps: mixing the obtained product material liquid with a saturated aqueous sodium carbonate solution, subjecting the resulting mixed solution to an extraction with ethyl acetate, and subjecting the resulting organic phase to a washing with saturated brine, a drying with anhydrous sodium sulfate, a filtration, and a spin-drying in sequence to obtain a crude deprotected product. The obtained crude product could be directly used in the next reaction without further purification. A certain amount of the saturated aqueous sodium carbonate solution is used such that the pH value of the resulting mixed solution is in the range of 9-10. In some embodiments, the extraction is performed multiple times, and the specific extraction times are determined by TLC to confirm that there is no product in the water phase, and the organic phases obtained from multiple extractions are combined.

After obtaining the deprotected product, the deprotected product and 3-nitro-4-halobenzenesulfonamide are subjected to a condensation reaction to obtain a compound having a structure represented by formula V. In some embodiments of the present disclosure, the 3-nitro-4-halobenzenesulfonamide is 3-nitro-4-fluorobenzenesulfonamide. In some embodiments, the molar ratio of the deprotected product to 3-nitro-4-halobenzenesulfonamide is in the range of 1:(1.05-1.3), and more preferably 1:1.2.

In some embodiments of the present disclosure, the solvent for the condensation reaction is one or more of dichloromethane, N,N-dimethylformamide, and toluene, and more preferably N,N-dimethylformamide. In the present disclosure, there is no special requirement for the amount of solvent used in the condensation reaction, as long as the condensation reaction could proceed smoothly.

In some embodiments of the present disclosure, the condensation reaction is carried out under the action of an alkaline reagent. In some embodiments, the alkaline reagent is N,N-diisopropylethylamine and/or triethylamine. In some embodiments, the molar ratio of the deprotected product to the alkaline reagent is in the range of 1:(2.2-2.5), and more preferably 1:(2.3-2.4).

In specific embodiments of the present disclosure, it is preferable that the crude deprotected product obtained in the above scheme is dissolved in the solvent for the condensation reaction, and then an alkaline reagent and 3-nitro-4-halobenzenesulfonamide are added and the resulting mixture is subjected to a condensation reaction. In some embodiments of the present disclosure, TLC is used to monitor the completion of the reaction. In some embodiments, the reagent for TLC detection is ethyl acetate.

In some embodiments, after the condensation reaction is completed, the obtained product material liquid is subjected to a post-treatment to obtain a compound having a structure represented by formula V. In some embodiments of the present disclosure, the post-treatment includes the following steps: mixing the resulting product material liquid with water and filtering the resulting mixture to obtain a filter cake; washing the filter cake with water and spin-drying to obtain a dry solid; crushing the dry solid, and adding ethyl acetate therein, and beating, filtering the resulting slurry, and collecting the solid to obtain the compound having a structure represented by formula V. In some embodiments of the present disclosure, the beating is conducted at room temperature. In some embodiments, the beating is conducted for 2 h.

After obtaining the compound having a structure represented by formula V, the compound having a structure represented by formula V and the second reducing agent are subjected to a carbonyl reduction reaction under an acidic condition to obtain the key intermediate of ABT-737, having a structural formula represented by formula VI. In some embodiments of the present disclosure, the second reducing agent is a boron reducing agent. In some embodiments, the boron reducing agent is one or more of sodium borohydride, potassium borohydride, boron trifluoride, a boron trifluoride-sodium borohydride complex, borane dimethyl sulfide, and a borane-tetrahydrofuran solution. In some embodiments, the concentration of the borane-tetrahydrofuran solution is 1 mol/L. In some embodiments of the present disclosure, the borane is a commercially available product or self-prepared. In some embodiments, it is prepared by the following method: mixing sodium borohydride with anhydrous tetrahydrofuran, adding the boron trifluoride-tetrahydrofuran solution dropwise therein under the protection of nitrogen, and subjecting the resulting mixture to a reaction for 30 minutes after the dripping to obtain a borane material liquid, wherein the borane material liquid obtained could be used directly, without any treatment. In some embodiments of the present disclosure, the borane-tetrahydrofuran solution is a commercially available product. In some embodiments of the present disclosure, the molar ratio of the compound having a structure represented by formula V to the second reducing agent is in the range of 1:(1.5-2), and more preferably 1:(1.7-1.8).

In the present disclosure, the acidic condition is provided by an acidic reagent. In some embodiments, the acidic reagent includes hydrochloric acid and/or trifluoroacetic acid. In some embodiments, the acid concentration of the acidic reagent is 4-10 mol/L, and more preferably 6-10 mol/L. In some embodiments, the amount ratio of the acidic reagent to the compound having a structure represented by formula V is in the range of (2-3):1.

In the present disclosure, the carbonyl reduction reaction is specifically as follows: mixing a compound having a structure represented by formula V with a boron reducing agent, and subjecting the resulting mixture to a complexation reaction to obtain a boron complex; mixing the boron complex and an acidic reagent, and subjecting the resulting mixture to a hydrolysis reaction to obtain a compound having a structure represented by formula VI. In some embodiments, the complexation reaction is conducted at room temperature. In some embodiments, the complexation reaction is conducted for 20-24 h. In some embodiments, the hydrolysis reaction is conducted at 70-90° C., and more preferably 80° C. In some embodiments, the hydrolysis reaction is conducted for 3-5 h, and more preferably 4 h. In specific embodiments of the present disclosure, after the completion of the complexation reaction, methanol is added to quench the complexation reaction, and then hydrochloric acid is added and the resulting mixture is subjected to a hydrolysis reaction; during the complexation reaction, the compound having a structure represented by formula V is coordinated with the boron reducing agent, to obtain a boronoxyalkyl radical intermediate. The boronoxyalkyl radical intermediate captures a hydrogen ion under an acidic condition, and then detaches the boronoxy group, to obtain an amine compound, thereby realizing the reduction of the amide carbonyl group.

In some embodiments, after the carbonyl reduction reaction is completed, the obtained product material liquid is subjected to a post-treatment to obtain a key intermediate of ABT-737 (labeled as intermediate A). In some embodiments of the present disclosure, the post-treatment includes the following steps: after cooling the obtained product material liquid to room temperature, adding saturated sodium carbonate solution therein, adjusting the pH value of the obtained product material liquid to 9-10, then subjecting the obtained product material liquid to an extraction with ethyl acetate, and subjecting the obtained organic phase to a washing with saturated brine, a drying with anhydrous sodium sulfate, a filtration, a spin-drying, and a purification by column chromatography in sequence to obtain the key intermediate of ABT-737. In some embodiments of the present disclosure, the extraction is performed 2 times, and the organic phases obtained from the two extractions are combined. In some embodiments, the reagent for column chromatography is a mixed solvent of dichloromethane and methanol. In some embodiments, the volume ratio of dichloromethane to methanol in the mixed solvent is 20:1.

The present disclosure also provides another route to synthesize a key intermediate of ABT-737, steps (1) to (3) are the same as the above schemes, only after obtaining the compound having a structure represented by formula IV, the compound having a structure represented by formula IV is first subjected to a carbonyl group reduction reaction, then a deprotection reaction, and a condensation reaction Specifically, the above step (4) is replaced by step (4'), and step (5) is replaced by (5'):

(4') subjecting the compound having a structure represented by formula IV and a second reducing agent to a carbonyl group reduction reaction under an acidic condition to obtain a compound having a structure represented by formula V', formula V'

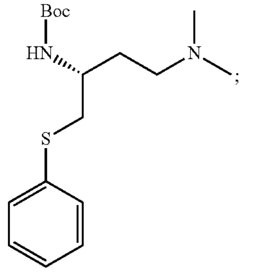

(5') subjecting the compound having a structure represented by formula V' and the deprotection reagent to a deprotection reaction to obtain a deprotected product, and subjecting the deprotected product to a condensation reaction with 3-nitro-4-halobenzenesulfonamide to obtain a key intermediate of ABT-737 having a structure represented by formula VI.

In the present disclosure, the compound having a structure represented by formula IV is subjected to a carbonyl reduction reaction with a second reducing agent under an acidic condition to obtain a compound having a structure represented by formula V'. In the present disclosure, the acidic condition is provided by an acidic reagent, and the types of the second reducing agent and the acidic reagent are the same as the above scheme, and will not be repeated here. The conditions and operation methods of the carbonyl reduction reaction are the same as the above scheme, and will not be repeated here. In some embodiments, the molar ratio of the compound having a structure represented by formula IV to the second reducing agent is in the range of 1:(1.5-2). In some embodiments, the molar ratio of the acidic reagent to the compound having a structure represented by formula IV is in the range of (2-3):1.

In some embodiments, after the carbonyl reduction reaction is completed, the obtained product liquid is subjected to a post-treatment to obtain a compound having a structure represented by formula V'. The post-treatment method is the same as the post-treatment method after the carbonyl reduction reaction in step (5) of the above scheme, and will not be repeated here.

After obtaining the compound having a structure represented by formula V', the compound having a structure represented by formula V' and a deprotection reagent are subjected to a deprotection reaction, and the obtained deprotected product is subjected to a condensation reaction with 3-nitro-4-halobenzenesulfonamide to obtain the key intermediate of ABT-737. In the present disclosure, the type of the deprotection reagent is the same as that of the above scheme, and will not be repeated here. The conditions of the deprotection reaction and the specific operation methods are consistent with those of the above scheme, and will not be repeated here. In some embodiments, the molar ratio of the compound having a structure represented by formula V' to the deprotection reagent is in the range of 1:(30-35), and the molar amount of the deprotection reagent is calculated as the molar amount of the solute.

In some embodiments, after the deprotection reaction is completed, the obtained product material liquid is subjected to a post-treatment to obtain the deprotected product. In some embodiments, the post-treatment method is the same as the post-treatment method after the completion of the deprotection reaction in step (4) of the above scheme, and will not be repeated here.

In some embodiments of the present disclosure, the specific type of the 3-nitro-4-halobenzenesulfonamide is consistent with that of the above scheme, and will not be repeated here. The conditions and specific operation methods of the condensation reaction are consistent with the above-mentioned scheme, and will not be repeated here. The post-treatment method after the completion of the condensation reaction is consistent with the post-treatment method after the completion of the condensation reaction in step (4) of the above scheme, and will not be repeated here.

The present disclosure also provides a method for preparing ABT-737, which includes the following steps:

preparing the key intermediate of ABT-737 according to the method as described in the above technical solution; and mixing the key intermediate of ABT-737 with 4-(4-((4'-chloro-[1,1'-biphenyl]-2-yl) methyl) piperazin-1-yl) benzoic acid, and subjecting the resulting mixture to a condensation reaction to obtain ABT-737, having a structural represented by formula VII, formula VII

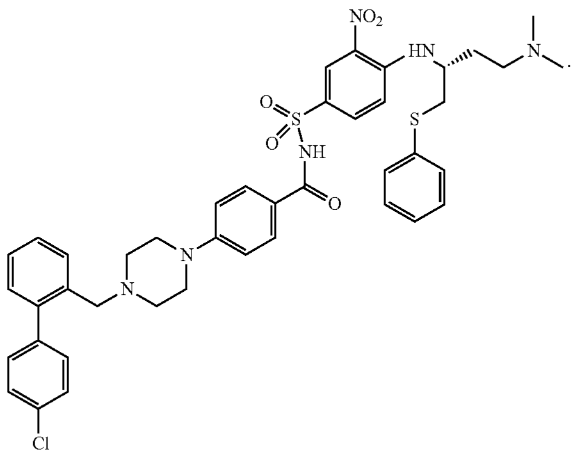

In some embodiments of the present disclosure, the condensation reaction is carried out under the actions of a condensing agent and a catalyst. In some embodiments, the condensing agent is dicyclohexylcarbodiimide and/or 3-(ethyliminomethylideneamino)-N,N-dimethylpropan-1-amine hydrochloride. In some embodiments, the catalyst is 4-dimethylaminopyridine and/or N,N-diisopropylethylamine. In some embodiments, the molar ratio of the key intermediate of ABT-737 (compound having a structure represented by formula VI), the condensing agent, and the catalyst is in the range of 1:(2-2.5):(2-2.5), and more preferably 1:2.1:2.1.

In some embodiments of the present disclosure, the molar ratio of the key intermediate of ABT-737 to 4-(4-((4'-chloro-[1,1'-biphenyl]-2-yl) methyl) piperazin-1-yl) benzoic acid is in the range of 1:(1.05-1.1).

In some embodiments of the present disclosure, the solvent for the condensation reaction is dichloromethane, 1,2 dichloroethane, N,N dimethylformamide, and more preferably dichloromethane. In some embodiments, the weight ratio of the solvent for the condensation reaction to the key intermediate of ABT-737 is in the range of (100-600):1, and more preferably (300-500):1.

In some embodiments of the present disclosure, the condensation reaction is conducted at room temperature. In some embodiments, the condensation reaction is conducted for 40-60 h, and more preferably 48-50 h.

In specific embodiments of the present disclosure, it is preferable that the key intermediate of ABT-737, 4-(4-((4'-chloro-[1,1'-biphenyl]-2-yl) methyl) piperazine-1-yl) benzoic acid are mixed with a solvent, and a condensing agent and a catalyst are added thereto in sequence under a stirring condition, and the resulting mixture is subjected to a condensation reaction.

In some embodiments, after the condensation reaction is completed, the obtained product material liquid is subjected to a post-treatment to obtain ABT-737. In some embodiments of the present disclosure, the post-treatment includes the following steps: mixing the obtained product material liquid and saturated ammonium chloride solution and layering the resulting mixture, subjecting the obtained organic layer to a washing with saturated brine, a drying with anhydrous sodium sulfate, a filtration, a drying and a purification by column chromatography in sequence to obtain a crude product;

dissolving the crude product with dichloromethane, adding the resulting solution dropwise to methyl tert-butyl ether to precipitate the solid product, stirring the precipitation system for 30 minutes, then filtering, and drying the resulting solid product to obtain ABT-737.

The technical solutions of the present disclosure will be described clearly and completely below in conjunction with the embodiments of the present disclosure.

The technical solutions of the present disclosure will be described clearly and completely below in conjunction with the embodiments of the present disclosure.

Example 1

The compound having a structure represented by formula I (in which, R is —$CH_3$) was used as the starting material, and the specific synthesis steps were as follows:

1) Preparation of the Compound Having a Structure Represented by Formula II (in which, R is —$CH_3$)

81.7 g (0.33 mol) of the compound having a structure represented by formula I was added to a three-necked flask, and 1600 mL of ethyl acetate was added thereto to dissolve the compound. After nitrogen replacement, the system was cooled to not higher than 0° C. 41.8 g (0.363 mol) of N-hydroxysuccinimide was added thereto in the open. The solution of dicyclohexylcarbodiimid in ethyl acetate (which was formed by dissolving 75 g (0.363 mol) of dicyclohexylcarbodiimide in 250 mL of ethyl acetate) was added dropwise thereto. The resulting mixture was maintained at a temperature of ~5° C. to 0° C., with the whole system turbid, and then subjected to a reaction at room temperature for 24 h. The disappearance of the raw materials was confirmed by TLC (dichloromethane:methanol:acetic acid=4 mL:0.2 mL:0.1 mL). The resulting product material liquid was filtered through diatomite. The filtrate was washed with 800 mL of saturated sodium carbonate solution, and the resulting mixture was layered. The aqueous layer was subjected to an extraction once with 300 mL of ethyl acetate. The organic phase was subjected to a washing with 500 mL of saturated brine, a drying with anhydrous sodium sulfate, a filtration, and a spin-drying, obtaining the active ester.

720 mL of tetrahydrofuran and 96 mL of water were added to a reaction flask. 20 g (0.529 mol) of sodium borohydride was added thereto under an ice bath condition, and they were stirred, obtaining a sodium borohydride solution. The obtained active ester was dissolved in 200 mL of THF, and the resulting solution was added dropwise to the prepared sodium borohydride solution at a temperature of 0° C. to 10° C. After the completion of dripping, the resulting mixture was subjected to a reaction for 5 min. After confirming the completion reaction of the active ester by TLC (reagent used was dichloromethane-methanol mixed solvent, and the volume ratio of dichloromethane to methanol was 20:1), 300 mL of saturated ammonium chloride aqueous solution was added to quench the reaction. The product material liquid was subjected to an extraction twice with 500 mL of ethyl acetate, and the organic phases were combined and washed with 300 mL of saturated brine, dried with anhydrous sodium sulfate, then spin-dried, and purified by column chromatography (petroleum ether:ethyl acetate=3:1), obtaining 51 g of the compound having a structure represented by formula II, with a yield of 66%.

2) Preparation of the Compound Having a Structure Represented by Formula III 51 g (0.219 mol) of the compound having a structure represented by formula II was added to a reaction flask, and 1.2 L of toluene was added thereto to dissolve the compound. 71.6 g (0.329 mol) of diphenyl disulfide and 66 g (0.329 mol) of tributylphosphine were added thereto in sequence, and the atmosphere was replaced with nitrogen. The resulting mixture was subjected to an airtight reaction at 80° C. in an oil bath for 18 h. The completion of the reaction was confirmed by using TLC (reagent used was a dichloromethane-methanol mixed solvent, and the volume ratio of dichloromethane to methanol was 20:1). Toluene was removed by concentrating, and the concentrated product was purified by column chromatography (a volume ratio of petroleum ether to ethyl acetate being 10:1), obtaining 62 g of the compound having a structure represented by formula III, with a yield of 87.7%.

3) Preparation of the Compound Having a Structure Represented by Formula IV 62 g (0.191 mol) of the compound having a structure represented by formula III, 900 mL of tetrahydrofuran, 300 mL of methanol, and 300 mL of water were added in sequence to a reaction flask. After dissolving, 32 g (0.572 mol) of lithium hydroxide monohydrate was added thereto, and the resulting mixture was stirred at room temperature for 24 h. The completion of the reaction was confirmed by TLC (reagent used was petroleum ether-ethyl acetate mixed solvent, and the volume ratio of petroleum ether to ethyl acetate was 2:1), and the reaction solution was then poured into 2 L of saturated sodium dihydrogen phosphate aqueous solution. The resulting mixture was subjected to an extraction three times with 500 mL of ethyl acetate. The organic phases were combined, washed with 500 mL of saturated brine, dried with anhydrous sodium sulfate, and spin-dried, obtaining the hydrolysate.

170 g (0.381 mol) of 2 mol/L dimethylamine-tetrahydrofuran solution was added to the spin-dried hydrolysate, and 73 g (0.381 mol) of 3-(ethyliminomethylideneamino)-N,N-dimethylpropan-1-amine hydrochloride and 23.3 g (0.191 mol) of 4-dimethylaminopyridine were added thereto, and 60 mL of dichloromethane was added. The resulting mixture was subjected to a reaction at room temperature for 24 h. The complete consumption of the raw material was confirmed by using TLC (dichloromethane:methanol:acetic acid=4 mL:0.2 mL:0.1 mL). 300 mL (0.3 mol) of 1 mol/L aqueous hydrochloric acid solution was added to the product material liquid for washing, and the organic phase was collected after layering. The obtained organic phase was washed with 300 mL of saturated brine, dried with anhydrous sodium sulfate, filtered and concentrated. The concentrated product was purified by column chromatography (petroleum ether:ethyl acetate=2:1), obtaining 60 g of the compound having a structure represented by formula IV with the yield of 92.5%.

4) Preparation of the Compound Having a Structure Represented by Formula V 60 g (0.177 mol) of the compound having a structure represented by formula IV, 1.5 L of dioxane, and 1.5 L of 4 mol/L hydrochloric acid were added into a three-necked flask, and the resulting mixture was subjected to a reaction at room temperature for 2 h. After confirming the complete consumption of the raw materials, the reaction solution was poured into 3 L of saturated aqueous sodium carbonate solution, and the pH value of the mixture was measured to be 9-10. The mixture was subjected to an extraction with 1 L of ethyl acetate several times until there was no product in the aqueous phase, which was confirmed by TLC. The organic phases were combined, then washed with 2 L of saturated brine, dried with anhydrous sodium sulfate, filtered and spin-dried, obtaining a crude product.

The obtained crude product was added to 500 mL of N,N-dimethylformamide, and dissolved therein. 57 g (0.443 mol) of N,N-diisopropylethylamine and 46.8 g (0.213 mol) of 3-nitro-4-fluorobenzenesulfonamide were added thereto. The resulting mixture was subjected to a reaction at room temperature for 24 h. After confirming the completion of the reaction by TLC (ethyl acetate), the reaction solution was poured into 3 L of water and filtered. The filter cake was washed with water, and the washed solid was collected and spin-dried. The dried solid obtained was crushed. 300 mL of ethyl acetate was added to the crushed solid, and they were stirred and beaten at room temperature for 2 hours, and filtered. The product was collected, obtaining 68 g of the compound having a structure represented by formula V with a yield of 87.5%.

5) Preparation of the Compound Having a Structure Represented by Formula VI (Intermediate A)

3.1 g (0.082 mol) of sodium borohydride was added to a reaction flask, and 100 mL of anhydrous tetrahydrofuran was added thereto. 16 g (0.114 mol) of boron trifluoride-tetrahydrofuran solution was added dropwise under the protection of nitrogen. After the completion of the dripping, the resulting mixture was subjected to a reaction for 30 min. The solution of the compound having a structure represented by formula V in tetrahydrofuran (which is formed by dissolving 20 g (0.046 mol) of the compound having a structure represented by formula V in 100 mL of tetrahydrofuran) was added dropwise thereto, and a large number of bubbles were generated during the process. The resulting reaction system was placed in an oil bath at 25° C., and subjected to a reaction for 24 h. After the reaction raw materials was completely consumed, 30 mL of methanol was added to quench the reaction. When there were no bubbles, 30 mL of concentrated hydrochloric acid was added thereto. The resulting system was heated to 80° C., then refluxed for 4 h, and cooled to room temperature. 200 mL of saturated sodium carbonate was added thereto to adjust the pH value to 9-10, and the resulting mixture was subjected to an extraction twice with 200 mL of ethyl acetate. The organic phase was washed with 200 mL of saturated brine, dried with anhydrous sodium sulfate, then filtered, and spin-dried in sequence. The spin-dried product mixture was purified by column chromatography (dichloromethane:methanol=20:1). 15 g of the product was collected (the key intermediate of ABT-737, compound having a structure represented by formula VI), with the yield of 77%.

6) Preparation of the Compound Having a Structure Represented by Formula VII 10 g (23.6 mmol) of the compound having a structure represented by formula VI and 10.5 g (25.8 mmol) of 4-(4-((4'-chloro-[1,1'-biphenyl]-2-yl)methyppiperazine-1-yl) benzoic acid were added into a reaction flask. 5000 mL of dichloromethane was then added. 6 g (49.1 mmol) of 4-dimethylaminopyridine was added under a stirring condition. After stirring to be clear, 9.48 g (49.5 mmol) of 3-(ethyliminomethylideneamino)-N,N-dimethylpropan-1-amine hydrochloride was added. The resulting mixture was subjected to a reaction at room temperature for 48 h. After the completion of reaction, 1000 mL of saturated ammonium chloride was added to the system to wash, and the resulting mixture was layered. The obtained organic phase was washed with 1000 mL of saturated brine, dried with anhydrous sodium sulfate, filtered and spin-dried. The spin-dried product mixture was purified by column chromatography (dichloromethane:methanol=20:1), obtaining 12 g of crude product.

The obtained crude product was dissolved in 120 mL of dichloromethane, and the resulting solution was then slowly added dropwise to 120 mL of methyl tert-butyl ether. A solid was precipitated out. After stirring for 30 minutes, the resulting mixture was filtered, and the solid was collected, and dried, obtaining 10.5 g of the compound having a structure represented by formula VII, with the purity of 99.1% and the yield of 55%.

Example 2

The compound having a structure represented by formula I (in which, R is —$CH_3$) was used as the starting material, and the specific synthesis steps were as follows:

1) Preparation of the Compound Having a Structure Represented by Formula II (in which, R is —$CH_3$)

35 g (0.121 mol) of the compound having a structure represented by formula I was added to a three-necked flask, and 700 mL of ethyl acetate was added thereto to dissolve the compound. Under the protection of nitrogen, the system was cooled to about 0° C. 15.3 g (0.133 mol) of N-hydroxysuccinimide was added thereto, then the solution of dicyclohexylcarbodiimide in ethyl acetate (which was formed by dissolving 27.4 g (0.133 mol) of dicyclohexylcarbodiimide in 140 mL of ethyl acetate) was then added dropwise thereto. The resulting mixture was maintained at a temperature of −5° C. to 0° C. The ice bath was removed, and the resulting system was subjected to a reaction at room temperature for 24 h. The disappearance of the raw materials was confirmed by TLC. The resulting product material liquid was filtered through diatomite, and the filter cake was washed with ethyl acetate. The filtrate was washed with 300 mL of saturated sodium carbonate solution, and the resulting liquid was subjected to an extraction once with 200 mL of ethyl acetate. The organic phase was combined and washed with 200 mL of saturated brine, dried with anhydrous sodium sulfate, filtered and spin-dried, obtaining the crude active ester.

300 mL of tetrahydrofuran and 40 mL of water were added to another reaction flask. 7.3 g (0.194 mol) of sodium borohydride was added thereto under an ice bath condition. They were stirred, obtaining a sodium borohydride solution. The obtained crude active ester was dissolved in 100 mL of THF, and the resulting solution was added dropwise to the prepared sodium borohydride solution. After the completion of dripping, the resulting mixture was stirred at low temperature for 10 min. After confirming the completion reaction of the active ester, 100 mL of saturated ammonium chloride aqueous solution was added thereto to quench the reaction. 200 mL of ethyl acetate was used to extract the product material liquid twice, and the organic phases were combined and washed with 200 mL of saturated brine, then subjected to a drying with anhydrous sodium sulfate, a spin-drying, and a purification by column chromatography (petroleum ether:ethyl acetate=3:1) in sequence, obtaining 20.4 g of the compound having a structure represented by formula II, with a yield of 61.2%.

2) Preparation of the Compound Having a Structure Represented by Formula III 20 g (0.073 mol) of the compound having a structure represented by formula II was added to a reaction flask, and 800 mL of toluene was added thereto to dissolve the compound. 23.8 g (0.109 mol) of diphenyl disulfide and 22 g (0.109 mol) of tributylphosphine were added thereto, and the atmosphere was replaced with nitrogen. The resulting mixture was subjected to a reaction at 80° C. in an oil bath for 18 h. TLC (dichloromethane:methanol=20:1) was used to confirm the completion of the reaction. The resulting product material liquid was concentrated, and the concentrated product was purified by column chromatography (petroleum ether:ethyl acetate=10:1), obtaining 22.8 g of the compound having a structure represented by formula III, with a yield of 85.5%.

3) Preparation of the Compound Having a Structure Represented by Formula IV 22 g (0.06 mol) of the compound having a structure represented by formula III, 400 mL of ethanol, and 200 mL of water were added in sequence to a reaction flask. After dissolving to be clear, 9.6 g (0.24 mol) of sodium hydroxide was added thereto, and the resulting mixture was stirred at room temperature for 24 h. After the completion of the reaction, the reaction solution was poured into 500 L of saturated sodium dihydrogen phosphate aqueous solution. The resulting mixture was then subjected to an extraction three times with 300 mL of ethyl acetate. The organic phases were combined, washed with 200 mL of saturated brine, dried with anhydrous sodium sulfate, and spin-dried, obtaining the hydrolysate.

60 mL (0.12 mol) of 2 mol/L dimethylamine-tetrahydrofuran solution was added to the spin-dried hydrolysate. 23 g (0.12 mol) of 3-(ethyliminomethylideneamino)-N,N-dimethylpropan-1-amine hydrochloride and 7.3 g (0.06 mol) of 4-dimethylaminopyridine were then added thereto. 20 mL of dichloromethane was then added thereto, and the resulting mixture was subjected to a reaction at room temperature for 24 h. The complete consumption of the raw material was confirmed by TLC (the volume ratio of dichloromethane, methanol, and acetic acid of 4:0.2:0.1). 100 mL (0.1 mol) of 1 mol/L aqueous hydrochloric acid solution was added to the product material liquid for washing, and the organic phase was collected after layering. The obtained organic phase was washed with 100 mL of saturated brine, dried with anhydrous sodium sulfate, filtered and concentrated. The concentrated product was purified by column chromatography (petroleum ether:ethyl acetate=2:1), obtaining 18.4 g of the compound having a structure represented by formula IV, with the yield of 90.8%.

4) Preparation of the Compound Having a Structure Represented by Formula V 15 g (0.044 mol) of the compound having a structure represented by formula IV, 375 mL of dioxane, and 375 mL of 4 mol/L hydrochloric acid were added into a three-necked flask. The resulting mixture was subjected to a reaction at room temperature for 2 h. After confirming the complete consumption of the raw materials, the reaction solution was poured into 800 mL of saturated aqueous sodium carbonate solution, and the pH value of the mixture was measured to be 9-10. The mixture was subjected to an extraction with 300 mL of ethyl acetate several times until there was no product in the aqueous phase, as confirmed by TLC. The organic phases were washed with 800 mL of saturated brine, dried with anhydrous sodium sulfate, filtered and spin-dried, obtaining a crude product.

The obtained crude product was added to 130 mL of N,N-dimethylformamide, and dissolved therein. 14.2 g (0.11 mol) of N,N-diisopropylethylamine and 11.7 g (0.053 mol) of 3-nitro-4-fluorobenzenesulfonamide were then added thereto. The resulting mixture was subjected to a reaction at room temperature for 24 h. After confirming the completion of the reaction by TLC (ethyl acetate), the reaction solution was poured into 800 mL of water and filtered, and the filter cake was washed with water. The washed solid was collected and spin-dried. The dried solid obtained was crushed, and 100 mL of ethyl acetate was then added thereto. The resulting mixture was stirred at room temperature for 2 hours, and filtered. The product was collected, obtaining 17.2 g of the compound having a structure represented by formula V with a yield of 89%.

5) Preparation of the Intermediate A 10 g (0.023 mol) of the compound having a structure represented by formula V was added to a reaction flask, and 40 mL of 1 mol/L boron-tetrahydrofuran solution was injected thereto by using a syringe under the protection of nitrogen. The resulting mixture was subjected to a reaction in an oil bath at 25° C. for 24 h. After the complete consumption of the raw materials, 15 mL of methanol was added to quench the reaction. When there were no bubbles, 10 mL of concentrated hydrochloric acid was added thereto, and the resulting system was heated to 80° C., refluxed for 4 h, and then cooled to room temperature. 100 mL of saturated sodium carbonate was added to adjust the pH value to 9-10. The resulting mixture was subjected to an extraction twice with 100 mL of ethyl acetate. The organic phase was washed with 100 mL of saturated brine, dried with anhydrous sodium sulfate, then filtered, spin-dried, and purified by column chromatography (dichloromethane:methanol=20:1), obtaining 6.58 g of the product (the key intermediate of ABT-737, compound having a structure represented by formula VI) with the yield of 68%.

6) Preparation of the Compound Having a Structure Represented by Formula VII 5.6 g (13.2 mmol) of the compound having a structure represented by formula VI and 5.9 g (14.5 mmol) of 4-(4-((4'-chloro-[1,1'-biphenyl]-2-yl)methyl)piperazine-1-yl) benzoic acid were added into a reaction flask. 2800 mL of dichloromethane was then added thereto. 3.38 g (27.7 mmol) of 4-dimethylaminopyridine was added thereto under a stirring condition. After stirring to be clear, 5.31 g (27.7 mmol) of 3-(ethyliminomethylideneamino)-N,N-dimethyl-propan-1-amine hydrochloride was added thereto. The resulting system was subjected to a reaction at room temperature for 48 h. After the completion of reaction, 800 mL of saturated ammonium chloride was added to the system to wash. The resulting mixture was layered. The organic phase was washed with 800 mL of saturated brine, dried with anhydrous sodium sulfate, filtered and spin-dried. The spin-dried product mixture was purified by column chromatography (dichloromethane:methanol=20:1), obtaining 6.5 g of crude product.

The obtained crude product was dissolved in 70 mL of dichloromethane, and the resulting solution was then slowly added dropwise to 70 mL of methyl tert-butyl ether.

A solid was precipitated out. After stirring for 30 min, the resulting mixture was filtered, and the solid was collected, and dried, obtaining 6.2 g of the compound having a structure represented by formula VII with the purity of 99.2% and the yield of 58%.

Example 3

The compound having a structure represented by formula I (in which, R is —$CH_3$) was used as the starting material, and the specific synthesis steps were as follows:

1) Preparation of the Compound Having a Structure Represented by Formula II (in which, R is —$CH_3$)

55 g (0.22 mol) of the compound having a structure represented by formula I was added to a three-necked flask, and 1000 mL of ethyl acetate was added thereto to dissolve the compound. The atmosphere was replaced with nitrogen, and the system was cooled to not higher than 0° C. 27.9 g (0.242 mol) of N-hydroxysuccinimide was added thereto in the open, and then the solution of dicyclohexylcarbodiimide in ethyl acetate (which is formed by dissolving 50 g (0.242 mol) of dicyclohexylcarbodiimide in 160 mL of ethyl acetate) was added thereto dropwise. The resulting mixture was maintained at a temperature of −5° C. to 0° C., with the whole system turbid, and then subjected to a reaction at room temperature for 24 h. The disappearance of the raw materials was confirmed by TLC (dichloromethane:methanol:acetic acid=4:0.2:0.1). The resulting product material liquid was filtered through diatomite. The filtrate was washed with 500 mL of saturated sodium carbonate solution, and subjected to an extraction once with 200 mL of ethyl acetate. The organic phases were combined and washed with 400 mL of saturated brine, dried with anhydrous sodium sulfate, filtered and spin-dried, obtaining the active ester.

480 mL of tetrahydrofuran and 65 mL of water were added to a reaction flask. 13.6 g (0.36 mol) of sodium borohydride was added thereto under an ice bath condition, and the resulting mixture was stirred. The obtained active ester was dissolved in 150 mL of THF, and the resulting solution was added dropwise to the prepared sodium borohydride solution at a controlled temperature of 0° C.-10° C. After the completion of dripping, the resulting mixture was subjected to a reaction for 5 min. After confirming the completion reaction of the intermediate state by TLC (dichloromethane:methanol=20:1 or dichloromethane:ethyl acetate=3:2), 200 mL of saturated ammonium chloride aqueous solution was added to quench the reaction. The product material liquid was subjected to an extraction with 300 mL of ethyl acetate twice, and the organic phases were combined and washed with 200 mL of saturated brine, dried with anhydrous sodium sulfate, and then spin-dried. The resulting product mixture was purified by column chromatography, obtaining 33.7 g of the compound having a structure represented by formula II, with a yield of 65%.

2) Preparation of the Compound Having a Structure Represented by Formula III 30 g (0.129 mol) of the compound having a structure represented by formula II was added to a reaction flask, and 750 mL of toluene was added thereto to dissolve the compound. 42 g (0.193 mol) of diphenyl disulfide and 39 g (0.193 mol) of tributylphosphine were then added in sequence. The atmosphere was replaced with nitrogen, and the resulting mixture was subjected to a reaction in an oil bath at 80° C. for 18 h, advantageously in a sealed condition. The completion of the reaction was confirmed by TLC (dichloromethane:methanol=20:1). Toluene was removed by concentrating. The concentrated product was purified by column chromatography, obtaining 37.2 g of the compound having a structure represented by formula III, with a yield of 89%.

3) Preparation of the Compound Having a Structure Represented by Formula IV 31 g (0.095 mol) of the compound having a structure represented by formula III, 450 mL of tetrahydrofuran, 150 mL of methanol, and 150 mL of water were added in sequence to a reaction flask. After dissolving to be clear, 16 g (0.286 mol) of lithium hydroxide monohydrate was added thereto, and the resulting mixture was stirred at room temperature for 24 h. The completion of the reaction was confirmed by TLC (petroleum ether:ethyl acetate=2:1) and the reaction solution was then poured into 500 L of saturated sodium dihydrogen phosphate aqueous solution. The resulting mixture was subjected to an extraction three times with 300 mL of ethyl acetate. The organic phases were combined, washed with 300 mL of saturated brine, dried with anhydrous sodium sulfate, and spin-dried, obtaining the hydrolysate.

85 g (0.191 mol) of 2 mol/L dimethylamine-tetrahydrofuran solution was added to the spin-dried hydrolysate. 36.5 g (0.191 mol) of 3-(ethyliminomethylideneamino)-N,N-dimethylpropan-1-amine hydrochloride and 11.6 g (0.095 mol) of 4-dimethylaminopyridine were then added thereto. 30 mL of dichloromethane was then added thereto, and the resulting mixture was subjected to a reaction at room temperature for 24 h. The complete consumption of the raw material was confirmed by TLC (dichloromethane:methanol:acetic acid=4:0.2:0.1). 150 mL (0.3 mol) of 1 mol/L aqueous hydrochloric acid solution was added for washing, and the organic phase was collected after layering. The obtained organic phase was washed with 200 mL of saturated brine, dried with anhydrous sodium sulfate, filtered and concentrated. The concentrated product was purified by column chromatography, obtaining 29.3 g of the compound having a structure represented by formula IV, with the yield of 91%.

4) Preparation of the Compound Having a Structure Represented by Formula V'

5 g (0.133 mol) of sodium borohydride was added to a reaction flask. 200 mL of anhydrous tetrahydrofuran was then added. Under the protection of nitrogen, 25.9 g (0.185 mol) of boron trifluoride-tetrahydrofuran solution was added dropwise thereto. After the completion of dripping, the resulting system was subjected to a reaction for 30 min. The solution of the compound having a structure represented by formula IV in tetrahydrofuran (which was formed by dissolving 25 g (0.074 mol) of the compound having a structure represented by formula IV in 100 mL of tetrahydrofuran) was added dropwise therein, and a lot of bubbles were generated during the process. The resulting reaction system was placed in an oil bath at 25° C. for 24 h. After confirming the complete consumption of the raw materials, 40 mL of methanol was added to quench the reaction. When there were no bubbles, 40 mL of concentrated hydrochloric acid was added thereto. The resulting system was heated to 80° C., then refluxed for 4 h, and cooled to room temperature. 300 mL of saturated sodium carbonate was added to adjust the pH value to 9-10, and the resulting mixture was then subjected to an extraction twice with 300 mL of ethyl acetate. The organic phases were combined and washed with 300 mL of saturated brine, dried with anhydrous sodium sulfate, then filtered, and spin-dried. The resulting product mixture was purified by column chromatography, obtaining 18.8 g of the compound having a structure represented by formula V' with the yield of 78.5%.

5) Preparation of the Compound Having a Structure Represented by Formula VI 18.8 g (0.058 mol) of the compound having a structure represented by formula V', 470 mL of dioxane and 470 mL of 4 mol/L hydrochloric acid were added in a three-necked flask. The resulting mixture was subjected to a reaction at room temperature for 2 h. After confirming the complete consumption of the raw materials, the reaction solution was poured into 700 mL of saturated aqueous sodium carbonate solution, and the pH value was measured to be 9-10. The product material liquid was subjected to an extraction several times with 300 mL of ethyl acetate until there was no product in the aqueous phase, as confirmed by TLC. The organic phase was washed with 800 mL of saturated brine, dried with anhydrous sodium sulfate, filtered and spin-dried to get the crude product.

170 mL of N,N-dimethylformamide was added to dissolve the crude ammonia prepared above. 18.7 g (0.145 mol) of N,N-diisopropylethylamine and 15.4 g (0.07 mol) of 3-nitro-4-fluorobenzenesulfonamide were then added thereto. The resulting mixture was subjected to a reaction at room temperature for 24 h. After confirming the completion of the reaction by TLC (ethyl acetate), the reaction solution was poured into 700 mL of water. The resulting mixture was subjected to an extraction twice with 300 mL of ethyl acetate. The organic phase was washed with 300 mL of saturated brine, dried with anhydrous sodium sulfate, filtered and spin-dried. The spin-dried organic phase was purified by column chromatography, obtaining 21.1 g of the compound (intermediate A) having a structure represented by formula VI, with a yield of 85.8%.

6) Preparation of the Compound Having a Structure Represented by Formula VII 20 g (0.047 mol) of the compound having a structure represented by formula VI and 21 g (0.052 mol) of 4-(4-((4'-chloro-[1,1'-biphenyl]-2-yl)methyl)piperazine-1-yl) benzoic acid were added into a reaction flask. 1000 mL of dichloromethane was then added. 12 g (0.098 mol) of 4-dimethylaminopyridine was added under a stirring condition. After stirring to be clear, 19.2 g (0.1 mol) of 3-(ethyliminomethylideneamino)-N,N-dimethylpropan-1-amine hydrochloride was added thereto. The resulting system was subjected to a reaction at room temperature for 48 h. After the completion of the reaction, 500 mL of saturated ammonium chloride was added to the system to wash, and the resulting mixture was layered. The organic phase was washed with 500 mL of saturated brine, dried by anhydrous sodium sulfate, filtered and spin-dried. The spin-dried organic phase was purified by column chromatography, obtaining 26 g of crude product.

The obtained crude product was dissolved in 260 mL of dichloromethane, and the resulting solution was then slowly added dropwise to 260 mL of methyl tert-butyl ether. A solid was precipitated out. After stirring for 30 min, the resulting mixture was filtered, and the solid was collected, and dried, obtaining 20 g of the compound having a structure represented by formula VII with the purity of 99.1% and the yield of 52.3%.

Example 4

The compound having a structure represented by formula I (in which, R is

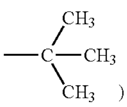

)

was used as the starting material, and the specific synthesis steps were as follows:

1) Preparation of the Compound Having a Structure Represented by Formula II (in which R is

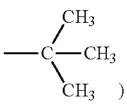

)

5 g (0.017 mol) of the compound having a structure represented by formula I was added into a three-necked flask, and 100 mL of ethyl acetate was added thereto to dissolve the compound. Under the protection of notrogen, the system was cooled to about 0° C. 2.2 g (0.019 mol) of N-hydroxysuccinimide was then added thereto. The solution of dicyclohexylcarbodiimide in ethyl acetate (which was formed by dissolving 3.9 g (0.019 mol) of dicyclohexylcarbodiimide in 20 mL of ethyl acetate) was then added dropwise at a controlled temperature of −5° C. to 0° C. The ice bath was removed, and the resulting system was subjected to a reaction at room temperature for 24 h. After confirming the disappearance of the raw materials by TLC, the resulting product material liquid was filtered through diatomite. The filter cake was washed with ethyl acetate. 50 mL of saturated sodium carbonate solution was added to the filtrate for washing, and the resulting mixture was subjected to an extraction once with 50 mL of ethyl acetate. The organic phases were combined and washed with 50 mL of saturated brine, dried with anhydrous sodium sulfate, filtered and spin-dried, obtaining the crude active ester.

45 mL of tetrahydrofuran and 6 mL of water were added to another reaction flask. 1.04 g (0.028 mol) of sodium borohydride was added thereto under an ice bath condition, and the resulting mixture was stirred, obtaining the sodium borohydride solution. The obtained crude active ester was dissolved in 15 mL of THF, and the resulting active ester solution was added dropwise to the prepared sodium borohydride solution. After the completion of dripping, the temperature was controlled to 0° C.-10° C., and the resulting mixture was stirred for 10 min. After confirming the complete consumption of the active ester, 20 mL of saturated ammonium chloride aqueous solution was added to quench the reaction. The product material liquid was subjected to an extraction twice with 50 mL of ethyl acetate. The organic phases were combined and washed with 50 mL of saturated brine, dried with anhydrous sodium sulfate, and spin-dried. The spin-dried organic phase was purified by column chromatography, obtaining 2.9 g of the compound having a structure represented by formula II, with a yield of 63%.

2) Preparation of the Compound Having a Structure Represented by Formula III 2 g (0.0073 mol) of the compound having a structure represented by formula II was added to a reaction flask, and 80 mL of toluene was added thereto to dissolve the compound. 2.4 g (0.01 mol) of diphenyl disulfide and 2.2 g (0.01 mol) of tributylphosphine were then added. The atmosphere was replaced with nitrogen. The resulting mixture was subjected to a reaction in an oil bath at 80° C. for 18 h. The completion of the reaction was confirmed by TLC (dichloromethane:methanol=20:1). The resulting product mixture was concentrated, and the concentrated product was purified by column chromatography, obtaining 2.2 g of the compound having a structure represented by formula III, with a yield of 82%.

3) Preparation of the Compound Having a Structure Represented by Formula IV 2.2 g (0.006 mol) of the compound having a structure represented by formula III, 40 mL of ethanol, and 20 mL of water were added in sequence to a reaction flask. After dissolving to be clear, 0.96 g (0.024 mol) of sodium hydroxide was added thereto, and the resulting mixture was stirred at room temperature for 24 h. After the completion of the reaction, the reaction solution was poured into 50 mL of saturated sodium dihydrogen phosphate aqueous solution. The resulting mixture was subjected to an extraction three times with 30 mL of ethyl acetate. The organic phases were combined, washed with 20 mL of saturated brine, dried with anhydrous sodium sulfate, and spin-dried, obtaining the intermediate.

6 mL (0.012 mol) of 2 mol/L dimethylamine-tetrahydrofuran solution was added to the spin-dried intermediate. 2.3 g (0.012 mol) of 3-(ethyliminomethylideneamino)-N,N-dimethylpropan-1-amine hydrochloride and 0.73 g (0.006 mol) of 4-dimethylaminopyridine were then added thereto. 2 mL of dichloromethane was then added thereto. The resulting mixture was subjected to a reaction at room temperature for 24 h. The complete consumption of the raw material was confirmed by TLC (dichloromethane:methanol:acetic acid=4:0.2:0.1). 10 mL (0.01 mol) of 1 mol/L aqueous hydrochloric acid solution was then added for washing, and the organic phase was collected after layering. The obtained organic phase was washed with 10 mL of saturated brine, dried with anhydrous sodium sulfate, filtered and concentrated. The concentrated product was purified by column chromatography, obtaining 1.77 g of the compound having a structure represented by formula IV, with the yield of 87.2%.

4) Preparation of the Compound Having a Structure Represented by Formula V'

0.3 g (0.008 mol) of sodium borohydride was added to a reaction flask, and 20 mL of anhydrous tetrahydrofuran was added thereto. Under the protection of nitrogen, 1.68 g (0.012 mol) of boron trifluoride-tetrahydrofuran solution was added dropwise therein. After the completion of dripping, the resulting system was subjected to a reaction for 30 min. The solution of the compound having a structure represented by formula IV in tetrahydrofuran (which was formed by dissolving 1.56 g (4.6 mmol) of the compound having a structure represented by formula IV in 10 mL tetrahydrofuran) was then added dropwise, and a lot of bubbles were generated during the process. The resulting system was placed in an oil bath at 25° C. and subjected to a reaction for 24 h. After the complete consumption of the raw materials, 2.5 mL of methanol was added to quench the reaction. When there were no bubbles, 2.5 mL of concentrated hydrochloric acid was added, and the resulting system was heated to 80° C., then refluxed for 4 h, and cooled to room temperature. 20 mL of saturated sodium carbonate was added to adjust the pH value to 9-10. The resulting mixture was subjected to an extraction twice with 30 mL of ethyl acetate. The organic phases were washed with 30 mL of saturated brine, dried with anhydrous sodium sulfate, filtered, and spin-dried. The spin-dried organic phase was purified by column chromatography, obtaining 1.13 g of the compound having a structure represented by formula V' with the yield of 76%.

5) Preparation of the Compound Having a Structure Represented by Formula VI 1 g (3.1 mmol) of the compound having a structure represented by formula V', 25 mL of dioxane, and 25 mL of 4 mol/L hydrochloric acid were added into a three-necked flask. The resulting mixture was subjected to a reaction at room temperature for 2 h. After confirming the complete consumption of the raw materials, the reaction solution was poured into 50 mL of saturated aqueous sodium carbonate solution, and the pH was measured to be alkaline (9-10). The product mixed liquid was subjected to an extraction with 30 mL of ethyl acetate several times until there was no product in the aqueous phase, as confirmed by TLC. The organic phase was washed with 50 mL of saturated brine, dried with anhydrous sodium sulfate, filtered and spin-dried to get the crude product.

10 mL of N,N-dimethylformamide was added to dissolve the crude product prepared above. 1 g (7.75 mmol) of N,N-diisopropylethylamine and 0.82 g (3.72 mol) of 3-nitro-4-fluorobenzenesulfonamide were then added. The resulting mixture was subjected to a reaction at room temperature for 24 h. After confirming the completion of the reaction by TLC (ethyl acetate), the reaction solution was poured into 50 mL of water. The resulting mixture was subjected to an extraction twice with 30 mL of ethyl acetate. The organic phase was washed with 30 mL of saturated brine, dried with anhydrous sodium sulfate, filtered and spin-dried. The spin-dried organic phase was purified by column chromatography, obtaining 1.16 g of the compound (intermediate A) having a structure represented by formula VI with a yield of 88%.

6) Preparation of the Compound Having a Structure Represented by Formula VII 1 g (2.36 mmol) of the compound having a structure represented by formula VI and 1.04 g (2.56 mmol) of 4-(4-((4'-chloro-[1,1'-biphenyl]-2-yl)methyppiperazine-1-yl) benzoic acid were added into a reaction flask, and then 50 mL of dichloromethane was added thereto. 0.6 g (4.92 mmol) of 4-dimethylaminopyridine was added thereto under a stirring condition. After stirring to be clear, 0.94 g (4.92 mmol) of 3-(ethyliminomethylideneamino)-N,N-dimethyl-propan-1-amine hydrochloride was added thereto. The resulting mixture was subjected to a reaction at room temperature for 48 h. After the completion of the reaction, 20 mL of saturated ammonium chloride was added to the system to wash, and the resulting mixture was layered. The organic phase was washed with 20 mL of saturated brine, dried with anhydrous sodium sulfate, filtered and spin-dried. The spin-dried organic phase was purified by column chromatography, obtaining 1.3 g of crude product.

The obtained crude product was dissolved in 15 mL of dichloromethane, and the resulting mixture was then slowly added dropwise to 15 mL of methyl tert-butyl ether. A solid was precipitated out. After stirring for 30 min, the resulting mixture was filtered, and the solid was collected, and dried, obtaining 1.1 g of the compound having a structure represented by formula VII with the purity of 99.2% and the yield of 59%.

The above are only the preferred embodiments of the present disclosure. It should be pointed out that for those of ordinary skill in the art, without departing from the principle of the present disclosure, several improvements and modifications could be made, and these improvements and modifications shall fall within the protection scope of the present disclosure.

What is claimed is:

1. A method for preparing a key intermediate of ABT-737, comprising (1) subjecting a compound having a structure represented by formula I and an activator to an esterification reaction to obtain an active ester, subjecting the active ester and a first reducing agent to a reduction reaction to obtain a compound having a structure represented by formula II, formula I

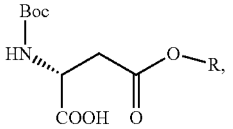

-continued formula II

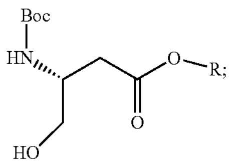

(2) subjecting the compound having a structure represented by formula II, a vulcanizing agent, and an organic phosphine to a vulcanization reaction to obtain a compound having a structure represented by formula III, wherein the vulcanizing agent comprises one or more selected from the group consisting of a thiophenol metal salt and diphenyl disulfide, formula III

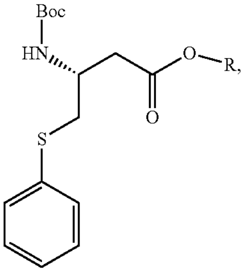

in formula I to formula III, R represents a chain alkyl group or cycloalkyl group;

(3) subjecting the compound having a structure represented by formula III to a hydrolysis reaction under an alkaline condition to obtain a hydrolysate, and subjecting the hydrolysate and dimethylamine to an amination reaction to obtain a compound having a structure represented by formula IV, formula IV

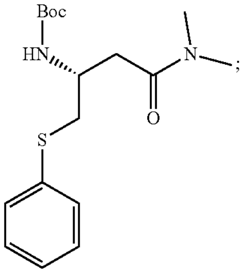

(4) subjecting the compound having a structure represented by formula IV to a deprotection reaction with a deprotection reagent to obtain a deprotected product, and subjecting the deprotected product to a condensation reaction with 3-nitro-4-halobenzenesulfonamide to obtain a compound having a structure represented by formula V, formula V

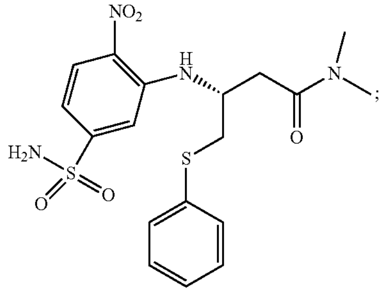

and (5) subjecting the compound having a structure represented by formula V and a second reducing agent to a carbonyl reduction reaction under an acidic condition to obtain the key intermediate of ABT-737 having a structure represented by formula VI, formula VI

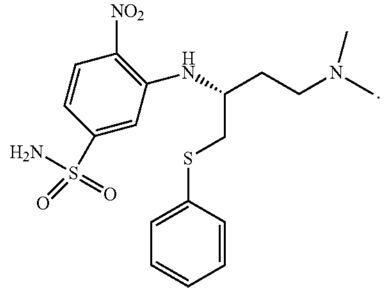

2. The method as claimed in claim 1, wherein the activator includes N-hydroxysuccinimide, isobutyl chloroformate, or a combination thereof; a molar ratio of the compound having a structure represented by formula I to the activator is in the range of 1:(1-1.2); and the esterification reaction is conducted at a temperature of −20° C. to 0° C. for 20-25 h.

3. The method as claimed in claim 1, wherein the esterification reaction is carried out under the conditions of a catalyst, and the catalyst is an organic amine; and a molar ratio of the compound having a structure represented by formula I to the catalyst is in the range of 1:(1.05-1.5).

4. The method as claimed in claim 1, wherein in step (1), the first reducing agent is a boron reducing agent; a molar ratio of the active ester to the first reducing agent is in the range of 1:(1.5-2);

the reduction reaction is carried out in a mixed solvent, and the mixed solvent comprises one or more selected from the group consisting of a tetrahydrofuran-water mixed solvent, a tetrahydrofuran-methanol mixed solvent, and a methanol-water mixed solvent; and the reduction reaction is conducted at a temperature of −5° C. to 20° C. for 5-20 min.

5. The method as claimed in claim 1, wherein a molar ratio of the compound having a structure represented by formula II to the vulcanizing agent is in the range of 1:(1.2-2);

the organic phosphine comprises one or more selected from the group consisting of tributyl phosphine, triphenyl phosphine, and tricarboxyethyl phosphine; a molar ratio of the compound having a structure represented by formula II to the organic phosphine is in the range of 1:(1.2-2); and the vulcanization reaction is conducted at a temperature of 70-85° C. for 15-20 h.

6. The method as claimed in claim 1, wherein in step (3), the alkaline condition is provided by an inorganic base; and a molar ratio of the compound having a structure represented by formula III to the inorganic base is in the range of 1:(2-4);

the hydrolysis reaction is conducted at room temperature for 20-24 h.

7. The method as claimed in claim 1, wherein the amination reaction is carried out under the conditions of a condensing agent and a catalyst, wherein the condensing agent comprises dicyclohexylcarbodiimide, 3-(ethyliminomethylideneamino)-N,N-dimethylpropan-1-amine hydrochloride, or a combination thereof, and the catalyst comprises 4-dimethylaminopyridine, N,N-diisopropylethylamine, or a combination thereof;

a molar ratio of the hydrolysate, the condensing agent, and the catalyst is in the range of 1:(1.8-2.5):(2-2.2);

a molar ratio of the hydrolysate to dimethylamine is in the range of 1:(1.5-2.5); and the amination reaction is conducted at room temperature for 20-30 h.

8. The method as claimed in claim 1, wherein the deprotection reagent is one or more selected from the group consisting of aqueous hydrochloric acid solution, hydrogen chloride-methanol solution, hydrogen chloride-ethyl acetate solution, and trifluoroacetic acid; and the deprotection reaction is conducted at room temperature for 2-5 h.

9. The method as claimed in claim 1, wherein a molar ratio of the deprotected product to 3-nitro-4-halobenzenesulfonamide is in the range of 1:(1.05-1.3); and the condensation reaction is conducted at a temperature of 20-30° C. for 20-30 h.

10. The method as claimed in claim 1, wherein in step (5), the second reducing agent is a boron reducing agent; the acidic condition is provided by an acidic reagent, and the acidic reagent comprises hydrochloric acid, trifluoroacetic acid, or a combination thereof; and the carbonyl reduction reaction is conducted specifically as follows: mixing a compound having a structure represented by formula V and a boron reducing agent, and subjecting the resulting mixture to a complexation reaction to obtain a boron complex; mixing the boron complex and an acidic reagent, and subjecting the resulting mixture to a hydrolysis reaction to obtain the compound having a structure represented by formula VI.

11. The method as claimed in claim 1, wherein step (4) is replaced by step (4'), and step (5) is replaced by (5'):

(4') under the actions of the second reducing agent and the acidic reagent, subjecting the compound having a structure represented by formula IV to a carbonyl reduction reaction to obtain a compound having a structure represented by formula V', formula V'

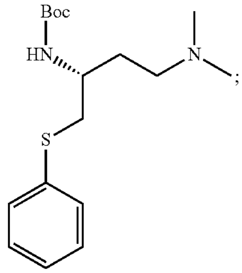

;

and (5') under the action of the deprotection reagent, subjecting the compound having a structure represented by formula V' to a deprotection reaction to obtain a deprotected product, and subjecting the deprotected product to a condensation reaction with 3-nitro-4-halobenzenesulfonamide to obtain the key intermediate of ABT-737.

12. The method as claimed in claim 2, wherein the esterification reaction is carried out under the conditions of a catalyst, and the catalyst is an organic amine; and a molar ratio of the compound having a structure represented by formula I to the catalyst is in the range of 1:(1.05-1.5).

* * * * *